(12) United States Patent
Ayers

(10) Patent No.: US 9,007,577 B2
(45) Date of Patent: Apr. 14, 2015

(54) ANALYTICAL INSTRUMENTATION IN HAZARDOUS ENVIRONMENTS VIA STATIC PRESSURIZATION

(71) Applicant: W. Stanley Ayers, Cary, NC (US)

(72) Inventor: W. Stanley Ayers, Cary, NC (US)

(73) Assignee: Mustard Tree Instruments, LLC, Research Triangle Park, NC (US)

( * ) Notice: Subject to any disclaimer, the term of this patent is extended or adjusted under 35 U.S.C. 154(b) by 0 days.

(21) Appl. No.: 14/065,876

(22) Filed: Oct. 29, 2013

(65) Prior Publication Data

US 2014/0118732 A1 May 1, 2014

Related U.S. Application Data

(60) Provisional application No. 61/720,339, filed on Oct. 30, 2012.

(51) Int. Cl.
| | |
|---|---|
| *G01J 3/44* | (2006.01) |
| *G01N 21/65* | (2006.01) |
| *G01J 3/02* | (2006.01) |
| *G01M 3/32* | (2006.01) |
| *G01M 3/26* | (2006.01) |

(52) U.S. Cl.
CPC ............... *G01N 21/65* (2013.01); *G01M 3/329* (2013.01); *G01M 3/26* (2013.01); *G01J 3/44* (2013.01); *G01N 2201/0227* (2013.01); *G01J 3/0286* (2013.01)

(58) Field of Classification Search
CPC ....... G01J 3/0286; G01N 21/01; G01N 21/65; G01N 1/24; G01N 2201/0236; C23C 16/455; G01M 3/26; G01M 3/3245; G01M 3/329; G01M 3/202
See application file for complete search history.

(56) References Cited

U.S. PATENT DOCUMENTS

| | | | |
|---|---|---|---|
| 4,845,977 A * | 7/1989 | Aarts ............................. 73/49.3 |
| 2003/0201606 A1* | 10/2003 | Shinozaki ...................... 277/301 |
| 2004/0222383 A1* | 11/2004 | Kawakami .................... 250/430 |
| 2006/0230826 A1* | 10/2006 | Nakamura et al. .............. 73/291 |
| 2007/0187634 A1* | 8/2007 | Sneh .......................... 251/30.01 |
| 2007/0291255 A1* | 12/2007 | Larsen et al. ................... 356/73 |
| 2008/0050538 A1* | 2/2008 | Hirata ........................... 427/585 |
| 2012/0060935 A1* | 3/2012 | Carter et al. .................... 137/14 |

* cited by examiner

*Primary Examiner* — Kara E Geisel
*Assistant Examiner* — Maurice Smith
(74) *Attorney, Agent, or Firm* — Coats & Bennett, PLLC

(57) ABSTRACT

An analytical instrument suitable for a use in a variety of industrial environments features a housing having a sealed primary chamber filled with a dry, inert gas at a first static pressure. An instrumentation system is disposed within the primary chamber, where fire hazard is eliminated by the inert gas. The housing additionally includes a reference chamber holding a gas a second pressure lower than the first pressure. One or more pressure switches, in pressure-sensing relationship with both chambers, is operative to interrupt the application of power to the instrumentation system if the differential between first and second pressures falls below a predetermined value. In this manner, the instrumentation system is rendered safe whenever the primary chamber is breached or otherwise loses inert gas pressure.

18 Claims, 2 Drawing Sheets

ANALYTICAL INSTRUMENTATION IN HAZARDOUS ENVIRONMENTS VIA STATIC PRESSURIZATION

This application claims priority to U.S. Provisional Patent Application Ser. No. 61/720,339, titled, "Analytical Instrumentation in Hazardous Environments via Static Pressurization," filed Oct. 30, 2012, the disclosure of which is incorporated herein by reference in its entirety.

FIELD OF INVENTION

The present invention relates generally to analytical instrumentation, and in particular to a compact system and method of analytical instrumentation in hazardous environments.

BACKGROUND

Analytical instrumentation refers to a broad variety of instruments that provide information on the composition of matter. Analytical instruments are important in many manufacturing and industrial processes, such as to assess/verify the purity of raw materials, to identify the progress or completion of chemical reactions, to determine defined stages in refining or other chemical transformation processes, to sort manufactured products by chemical purity, for quality control, and the like.

One type of analytical instrument that has application in a broad array of manufacturing and industrial processes is a Raman spectrometer. Raman spectroscopy is a method of ascertaining and verifying the molecular structures of materials. Raman spectroscopy relies on inelastic scattering, or Raman scattering, of monochromatic light, resulting in an energy shift in a portion of the photons scattered by a sample. From the shifted energy of the Raman scattered photons, vibrational modes characteristic to a specific molecular structure can be ascertained. In addition, by analytically assessing the relative intensity of Raman scattered photons, the concentration of a sample can be quantitatively determined.

The Raman effect occurs when light impinges upon a molecule and interacts with the electron cloud and the bonds of that molecule. For the spontaneous Raman effect, which is a form of light scattering, a photon excites the molecule from its ground state to a virtual energy state. The energy state is referred to as virtual since it is temporary, and not a discrete (real) energy state. When the molecule relaxes, it emits a photon and it returns to a different rotational or vibrational state. The difference in energy between the original state and this new state leads to a shift in the emitted photon's frequency away from the excitation wavelength.

If the final vibrational state of the molecule is more energetic than the initial state, then the emitted photon will be shifted to a lower frequency in order for the total energy of the system to remain balanced. This shift in frequency is known as a Stokes shift. If the final vibrational state is less energetic than the initial state, then the emitted photon will be shifted to a higher frequency, which is known as an Anti-Stokes shift. Raman scattering is an example of inelastic scattering because of the energy transfer between the photons and the molecules during their interaction.

The pattern of shifted frequencies is determined by the rotational and vibrational states of the sample, which are characteristic of the molecules. The chemical makeup of a sample may thus be determined by an analysis of the Raman scattering. In Raman spectroscopy, a sample is typically illuminated with a laser beam. Light from the illuminated spot is collected by lenses and analyzed. Wavelengths close to the laser line due to elastic Rayleigh scattering are blocked or filtered out, while chosen bands of the collected light are directed onto a detector. The spectra of these photons are analyzed to identify peaks resulting from concentrations of Stokes and Anti-Stokes shifted photons. The spectra are characteristic of the molecular structure of the sample, and the amplitude of the peaks may be analyzed to ascertain relative concentrations of identified molecules in the sample. Of course, Raman spectroscopy is just one of many types of analytical instrumentation useful in many manufacturing and industrial processes.

The environments in which many manufacturing and industrial processes take place are not conducive to, or present a hazard to, any type of electrical or electronic equipment, including analytical instrumentation. For example, many industrial environments present a fire hazard. The US National Fire Protection Association publishes NFPA code 70, also known as the National Electrical Code (NEC). The NEC defines three classes of fire hazardous conditions based on the type of fire hazard present: Class I (gas and vapor), Class II (dust), and Class III (fibers and flyings). Each Class is divided into Division 1 (hazardous condition normally present) and Division 2 (hazardous condition not normally present but may accidentally exist). The Classes are further subdivided into groups based on the specific material giving rise to the fire hazard.

Conventionally, electronic equipment operative in a NEC Class I Division 1 (C1D1) environment—for example, a petroleum refinery where flammable or explosive gases or vapors are normally present—is protected by actively purging oxygen from the equipment and replacing it with an inert gas. The equipment is located in a housing, and all air within the housing must be purged using an inert gas such as nitrogen a predetermined number of times (e.g., thrice), and then maintained with a dynamic positive pressure of the inert gas, relative to the surrounding atmosphere, prior to any electronics being activated. This ensures that the interior of the housing is non-incendive, and the electronics cannot cause a fire in the event of a spark, arc, overheating, or the like. The purge requires an external source of inert gas, such as a tank, and associated gas conduction lines, valves, pressure sensors, a controller, and the like. The dynamic, positive inert gas pressure is generally maintained by continued connection to the external inert gas tank, overcoming small leaks from the housing by applying a constant pressure of inert gas to the equipment. Such purging and dynamic pressure maintenance equipment is bulky, inconvenient, and expensive, and the purging process introduces delay in utilizing the electronic equipment.

Aside from fire hazard, many analytical instrumentals must operate in inhospitable environments, such as wet locations, or locations in which they are exposed to chemical drips, mists, or vapors. Protection of the electronics or optical systems in these instruments from such environmental hazards is important.

Analytical instruments are often deployed to monitor processes or production environments that are tightly regulated, such as pharmaceutical manufacturing. In such environments, it is valuable to be able to prove that an analytical instrument has not been tampered with, or modified to alter the reported results of a measurement. Additionally, the integrity of analytical equipment housings may be valuable, such as to verify that chemical contamination has not occurred, or to access the validity of warranty claims. A variety of tamper-proof and tamper-evident equipment housings and seals are known in the art. However, these functions increase the cost of the equipment, and may require special tools, chemical detectors, codes, and the like to effect the tamper-proof or tamper-evident function, which additionally add cost and complexity.

A particular concern with analytical instruments utilizing lasers, such as Raman spectrometers, is compliance with laser safety regulations. The American National Standard Institute publishes ANSI Z136 defining classes of lasers based on power and wavelength, and prescribing associated required safety measures, such as labeling and the use of safety goggles. Where high power lasers are employed, the laser source and optical paths may be carefully positioned and maintained to prevent or minimize interaction with the beam path, to mitigate the risk of eye injury or other laser hazard. Since access to the laser source could alter the laser beam path in a way that may result in violation of the applicable standards, analytical instruments utilizing powerful lasers typically include mechanical switches on the equipment housing, coupled to interlock circuits that cut off power to the laser source if the housing is opened. Both the switches and interlock circuitry add cost and complexity to the instrument.

Analytical instruments often include sensitive detectors or transducers, such as Charge Coupled Devices (CCD) in optical instruments, which are cooled to improve their sensitivity. For example, operation at lower temperature reduces the rate of natural thermal electron-hole formation in semiconductor materials. Thermal hole-electron pairs increase the shot noise and reduce the ultimate sensitivity of the detector. One hazard to cooling electronic circuits or subsystems is the condensation of water from warmer, ambient air. Condensation can damage a detector, cause short circuits in electronics, promote rust and corrosion, and the like. To combat condensation, cooled electronics conventionally must provide dehumidification, such as by purging the system with a dry gas, similar to the inert gas purge discussed above for fire hazard protection. Such dehumidification systems add bulk, cost, and complexity to analytical instruments.

The Background section of this document is provided to place embodiments of the present invention in technological and operational context, to assist those of skill in the art in understanding their scope and utility. Unless explicitly identified as such, no statement herein is admitted to be prior art merely by its inclusion in the Background section.

SUMMARY

The following presents a simplified summary of the disclosure in order to provide a basic understanding to those of skill in the art. This summary is not an extensive overview of the disclosure and is not intended to identify key/critical elements of embodiments of the invention or to delineate the scope of the invention. The sole purpose of this summary is to present some concepts disclosed herein in a simplified form as a prelude to the more detailed description that is presented later.

According to one or more embodiments described and claimed herein, an analytical instrument suitable for a use in a variety of industrial environments features a housing having a primary chamber filled with a dry, inert gas such as nitrogen, helium, argon, carbon dioxide, or the like. The primary chamber is pressurized at manufacture or routine service intervals, and maintains a positive static pressure of the inert gas throughout its operation. An instrumentation system (e.g., electronic, optical, electro-optical, electro-mechanical, or the like) is disposed within the primary chamber. One or more sealed, windowed ports allow emissions and observations, such as the emission of a laser beam and the collection of an optical signal, in the exemplary case of a Raman spectrometer. Because the instrumentation system is sealed in the primary chamber, it is protected from moisture and chemical drips, mists, or vapors.

The housing additionally includes a reference chamber holding a gas a pressure lower than that of the primary chamber. One or more pressure switches disposed between the primary and reference chamber, and in pressure sensing relationship with both chambers, control the application of power to the instrumentation system. If the pressure differential between the primary chamber and reference chamber falls below a predetermined level, power to the instrumentation system is interrupted.

Maintenance of a predetermined static positive pressure of inert gas in the primary chamber is thus a prerequisite to electrical activation of the instrumentation system. Stated differently, as soon as positive pressure of inert gas over the instrumentation system falls below the predetermined level, power is interrupted and the instrumentation system is shut down, eliminating any fire hazard. This eliminates the purging requirement of prior art systems for operation in NEC C1D1 environments (explosive gas or vapor normally present).

Restarting the instrumentation system following a pressure-loss shutdown may require authorization, such as cryptographic key maintained at a service center or by authorized service personnel. Accordingly, the system is safe from tampering, and its readings may be trusted in tightly regulated applications. Other tampering concerns, such as access that would void a warranty, are also eliminated. Laser safety is maintained in the event of a housing breach, since the laser source shuts down upon pressure loss and cannot be restarted without authorization (when safety-compliant optical beam containment can be verified). Because the inert gas has a low dew point, moisture cannot condense on the instrumentation system components due to cooling necessary to increase sensitivity or reduce thermal noise. The positive pressure of dry, inert gas may additionally be monitored by pressure sensors within primary chamber, and a log of pressure recorded over time. This provides an additional record of the primary chamber integrity, and may be used to monitor the loss of pressure, and predict a time at which a re-pressurization operation will be required.

One embodiment relates to an analytical instrument. The instrument includes a housing comprising a sealed primary chamber filled with an inert gas at a first pressure. The primary chamber is separated by a bulkhead from a reference chamber filled with gas at a second pressure. The second pressure is lower than the first pressure by a predetermined pressure differential. The instrument also includes an instrumentation system disposed in the primary chamber, and a power delivery network operative to provide electrical power to the instrumentation system. The instrument further includes a pressure switch disposed in the bulkhead between the primary and reference chambers. The pressure switch is connected to the power delivery network, and is operative to interrupt power to the instrumentation system if the pressure differential falls below the predetermined level.

Another embodiment relates to a method of operating an analytical instrument in a hazardous environment. An instrumentation system is provided in a sealed primary chamber of a housing; the primary chamber is filled with an inert gas at a first pressure. A pressure differential between the first pressure and a second pressure in a reference chamber of the housing is monitored. Power is applied to operate the instrumentation system. If the pressure differential is sensed to fall below a predetermined value, power to the instrumentation system is interrupted.

BRIEF DESCRIPTION OF THE DRAWINGS

The present invention will now be described more fully hereinafter with reference to the accompanying drawings, in which embodiments of the invention are shown. However, this invention should not be construed as limited to the embodiments set forth herein. Rather, these embodiments are provided so that this disclosure will be thorough and complete, and will fully convey the scope of the invention to those skilled in the art.

DETAILED DESCRIPTION

It should be understood at the outset that although illustrative implementations of one or more embodiments of the present disclosure are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

Figure 1:
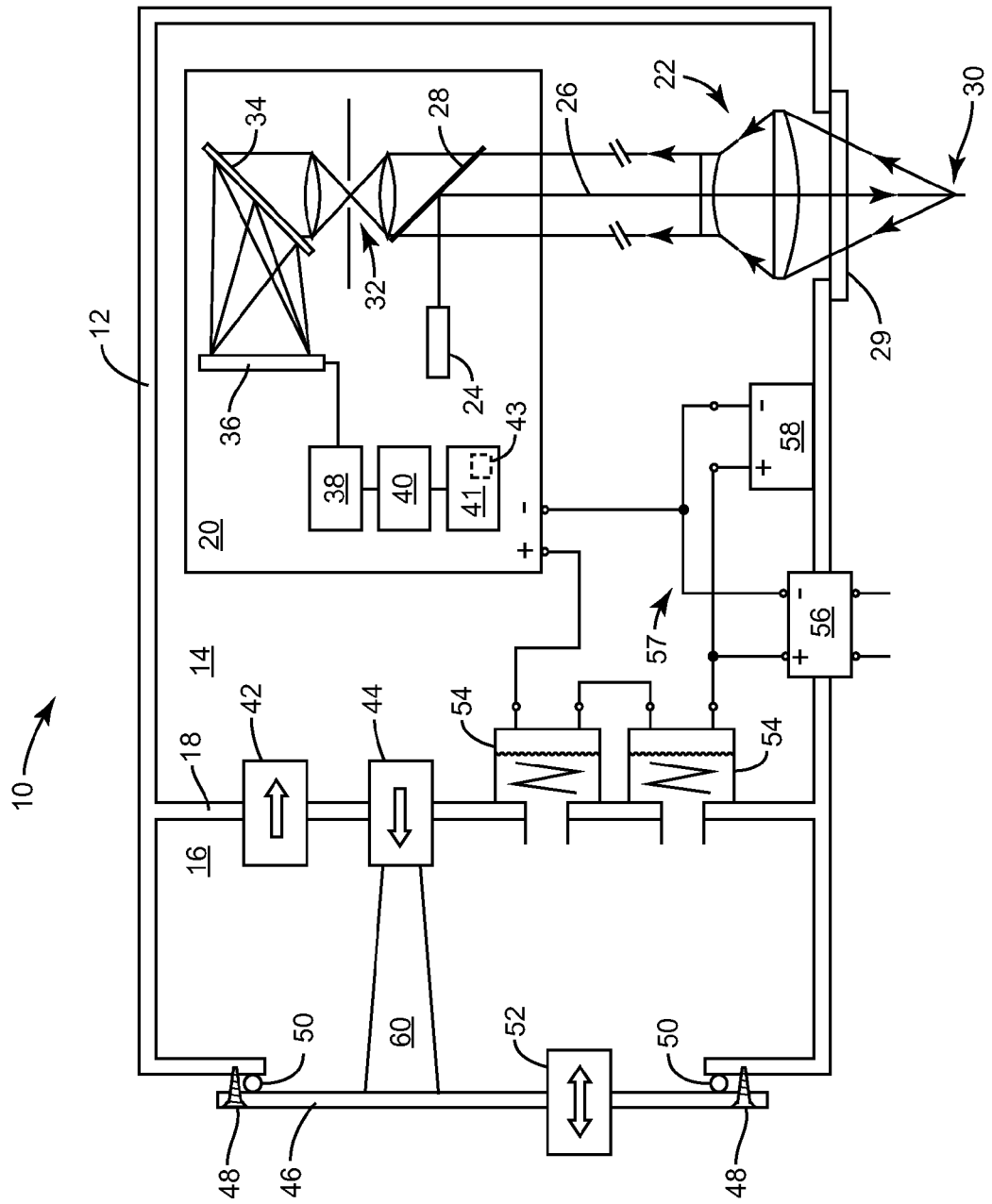
FIG. 1 is a section diagram of an analytical instrument according to one embodiment of the present invention.

FIG. 1 depicts a section view of an analytical instrument 10 in the form of a Raman spectrometer. The spectrometer is representative only and is used for discussion and explication herein. However, in general the present invention is not limited to spectroscopic, optical, or electro-optical systems. The analytical instrument 10 comprises a housing 12. The housing 12 is divided into a primary chamber 14 and a reference chamber 16. The chambers 14, 16 share a common bulkhead 18. As explained further herein, the primary chamber 14 contains an inert gas at a first pressure, and the reference chamber 16 contains a gas at a second pressure lower than the first pressure. An instrumentation system 20, such as Raman spectrometer, is disposed in the primary chamber 14. The instrumentation system 20 may additionally include components 22, such as part of an optical system.

Although not critical to the present invention, the Raman spectroscopy system 20 will be described, for the purpose of enabling those of skill in the art to practice embodiments of the present invention. A laser source 24 generates an excitation laser beam 26. The excitation beam 26 is reflected by a dichroic mirror 28, and directed toward a sample. The excitation beam 26 passes through an assembly 22 of lenses. The collimated excitation beam 26 has a small diameter compared to the lenses 22. It passes through the center of the lenses 22 where the excitation beam 26 is normal to the lens surfaces and experiences little refraction, thus remaining substantially collimated. Additionally, the excitation beam 26 has a very small "dot" of cross-section area, and the lenses 22 do little to focus or otherwise optically alter the excitation beam 26. The excitation beam 26 exits the housing 12 through a transparent window 29.

The lens assembly 22 has a fixed focus point 30 configured to collect Raman scattered photons from a sample, generated in response to the excitation beam 26. As one non-limiting example, the lens assembly 22 may comprise a two-element inverse Galilean Telescope lens system, comprising anti-reflection coated quartz elements. At the focal point 30 of the lens assembly 22, Raman scattering may be modeled as a point source optical phenomenon, with isotropic emission.

The Raman scattered photons are collected from the focal point 30 as an optical signal, the envelope of which is depicted in FIG. 1. This optical signal passes through the transparent window 29 and dichroic mirror 28, and is focused by lenses to a point, where it passes through a spectrometer aperture slit 32. The slit 32 isolates the interior of the spectrometer 20 (in particular, the detector 36) from extraneous photons.

A transmission grating 34 then directs the collected, Raman scattered photons to a detector 36. In one embodiment, the transmission grating 34 is a holographic transmission grating comprising a transparent window with periodic optical index variations, which diffract different wavelengths of light from a common input path into different angular output paths. In one embodiment, the holographic transmission grating 34 comprises a layer of transmissive material, such as dichromated gelatin, sealed between two protective glass or quartz plates. The phase of incident light is modulated, as it passes through the optically thick gelatin film, by the periodic stripes of harder and softer gelatin. In another embodiment, the transmission grating 34 comprises a "ruled" reflective grating, in which the depth of a surface relief pattern modulates the phase of the incident light. In all embodiments, the spacing of the periodic structure of the transmission grating 34 determines the spectral dispersion, or angular separation of wavelength components, in the diffracted light. In one embodiment, the detector 36 comprises a charge-coupled device (CCD) array. The detector 36 converts incident photonic energy to electrical signals, which are processed by readout electronics 38.

The spectroscopy data from the readout electronics 38 are analyzed by a signal processor 40, such as an appropriately programmed Digital Signal Processor (DSP) or other microprocessor, also operatively connected to memory 41. Data representing the processed Raman spectra may be stored, output to a display, transmitted across a wired or wireless network, or the like, as known in the art. In addition to analyzing Raman spectra data, the signal processor 40—or another processor (not shown in FIG. 1)—may additionally control the overall operation of the analytical instrument 10, including initialization, calibration, testing, automated data acquisition procedures, user interface operations, remote communications, and the like. The memory 41 may comprise any non-transient machine-readable media known in the art or that may be developed, including but not limited to magnetic media (e.g., floppy disc, hard disc drive, etc.), optical media (e.g., CD-ROM, DVD-ROM, etc.), solid state media (e.g., SRAM, DRAM, DDRAM, ROM, PROM, EPROM, Flash memory, etc.), or the like. The memory 41 is operative to store program instructions 43 operative to implement the functionality described herein, as well as general purpose control functions for analytical instrumentation, as well known in the art.

At manufacture, and possibly at periodic service intervals, the primary chamber 14 is purged of atmospheric air by an inert gas. As used herein the term "inert" means a gas that is chemically unreactive under normal conditions encountered in industrial and manufacturing environments. Examples of inert gases include molecular nitrogen ($N_2$) and noble gases such as helium (He), neon (Ne), argon (Ar), and the like. The inert gas is preferably dry, having a low dew point and hence unable to contain significant water vapor. After thorough purging, the primary chamber 14 is filled with the inert gas to a first pressure greater than atmospheric pressure. In one embodiment, the first pressure is at least 14 psig (pounds per square inch gauge). The inert gas is introduced, in one embodiment, through a one-way fill valve 42. Various purge valves (not shown) may be disposed in the housing 12, spaced away from the fill valve 42, to facilitate the purge operation. A safety valve 44, rated or set to somewhat higher than the desired first pressure, prevents inadvertent over-pressurization of the primary chamber 14.

The reference chamber 16 is filled with a gas at a second pressure lower than the first pressure of the primary chamber 14. In one embodiment, the reference chamber 16 contains atmospheric air, at atmospheric pressure (i.e., 0 psig). In other embodiments, the reference chamber 16 may be maintained at a pressure greater than 0 psig, but lower than the primary chamber 14 by a predetermined pressure differential. A cover or access panel 46 is secured to the walls of the reference chamber 16, such as by fasteners 48. In one embodiment, for added tamper resistance, the fasteners 48 may comprise security fasteners having a unique (or at least uncommon) keyway shape, requiring a corresponding shaped driver bit to remove. An O-ring 50, or similar deformable seal, may be used to seal the reference chamber 16 against atmospheric pressure in embodiments in which the reference chamber 16 is maintained at greater than 0 psig. Even in embodiments in which the reference chamber 16 is maintained at atmospheric pressure, it is advantageous to seal the reference chamber 16 against the exterior environment, for reasons discussed below. However, the cover 46 is not essential. In one embodiment (not shown), the reference chamber 16 is open to the exterior. Indeed, in one embodiment (not shown) the walls of the housing 12 defining the reference chamber 16 (other than the bulkhead 18) do not exist, and the reference chamber 16 is effectively the exterior environment.

In one embodiment, an equalization port 52 is disposed between the reference chamber 16 and the ambient atmosphere. The equalization port 52 may comprise a gas permeable membrane, or other element operative to exchange air but prevent the ingress of external moisture or contaminants. In embodiments in which the reference chamber 16 is maintained at atmospheric pressure, the equalization port 52 prevents inadvertent pressurization of the reference chamber 16, such as through slow leakage of gas from the primary chamber 14 through the safety valve 44, which would decrease the pressure differential between the primary chamber 14 and reference chamber 16.

Maintaining a positive pressure of inert gas in the primary chamber 14 is critical for safe operation of the instrumentation system 20 in a hazardous environment (e.g., NEC C1D1). According to embodiments of the present invention, one or more pressure switches 54 operate as an interlock between a power delivery network 57 and the instrumentation system 20. The switches 54 are operative to interrupt power delivered to the instrumentation system 20 immediately upon sensing that the differential pressure between the primary chamber 14 and reference chamber 16 falls below a predetermined level (indicating a loss in pressure of the inert gas in the primary chamber 14). Although only one pressure switch 54 will interrupt power to the instrumentation system 20, in one embodiment, two or more pressure switches 54 are connected in series for added reliability. In this embodiment, if one pressure switch 54 malfunctions and remains conductive when the differential pressure drops, another pressure switch 54 will open and interrupt the power.

In some embodiments, the power delivery network 57 comprises a sealed electrical connection 56, which connects to an external power source (not shown) appropriate to the instrumentation system 20. In some embodiments, the power delivery network 57 connects to an internal battery 58, sized and configured to provide power appropriate to the instrumentation system 20. In the embodiment depicted in FIG. 1, the power delivery network 57 connects a rechargeable internal battery 58 to the external power connection 56. Appropriate power control circuits (not shown) control the application of power to and from the battery 58, and to the instrumentation system 20.

Each pressure switch 54 (also known as a vacuum switch or diaphragm switch) includes two ports—one open to each of two different pressure environments—and an internal diaphragm separating the environments. The diaphragm carries one switch electrical contact. The diaphragm is biased to one side by a force (e.g., spring) that may be predetermined and specified as part of the switch rating, or may be adjustable. In a quiescent condition, a force on the diaphragm due to a pressure differential between the two pressure environments is exactly countered by the bias force. A change in the differential pressure then will move the diaphragm physically one direction or the other, making or breaking contact with a second switch contact to change the switch state, depending on the design and configuration of the switch 54. Pressure switches 54 may be configured as normally open or normally closed, and may be configured to change switch state due to an increase or decrease in the pressure differential.

In one embodiment, the pressure switches 54 are normally open, and are maintained in a closed state only by the pressure differential between the primary chamber 14 and reference chamber 16. If this pressure differential falls below a predetermined value—such as the rated or set value of the spring force supporting the diaphragm in each switch 54—at least one of the switches 54 will open, interrupting the provision of power to the instrumentation system 20. Thus, upon a loss of pressure of inert gas in the primary chamber 14, all electronics associated with the instrumentation system 20 are immediately shut down, eliminating any possibility of fire arising from flammable gas entering the primary chamber 14. Similarly, any laser source 24 is shut down immediately upon the primary chamber 14 being opened (causing a loss of pressure), preserving the laser safety features designed into the beam path control. Of course, the same functionality may be achieved by different configurations of the switches 54. Regardless of the configuration in any particular embodiment, it is a change of state (e.g., open-to-closed or closed-to-open) of a switch 54 due to a drop in the pressure differential between the primary chamber 14 and the reference chamber 16 that causes an interruption in the delivery of power to the analytical instrument 20.

In one embodiment, one or more internal pressure sensors (not shown) monitor the pressure in the primary chamber 14. Software, such as software 43 in memory 41, executing on a processor, such as the DSP 40 of the instrumentation system 20, may periodically take a reading from the pressure sensor(s), and maintain a log of the primary chamber 14 pressure. Analysis of this log may reveal a slow leak in pressure (e.g., through the safety valve 44). One benefit of such analysis is that the program may provide a prediction of the time remaining until the primary chamber 14 will need to be recharged with inert gas to prevent "tripping," or a change in state of the pressure switches 54. This feature adds to the reliability of the analytical instrument 10 by reducing number the times that the instrumentation system 20 will become inoperative due to a slow loss of pressure from the primary chamber 14. The pressure log will also reveal any tampering with the analytical instrument 10—e.g., by a gap in a series of periodic readings caused by loss of power to the DSP 40. Such tamper detection is useful for verifying the integrity of the analytical instrument 10 in tightly regulated environments, assessing the validity of warranty claims, and the like. In some embodiments, for further security, non-instrumentation data such as the pressure log may be encrypted using a public key, the corresponding private key being known only to the analytical instrument 10 manufacturer and its authorized service technicians. Software interlocks may additionally preclude restarting the instrumentation system 20 after a power interruption, without a cryptographic key. This would ensure that the analytical instrument 10 manufacturer has the opportunity to inspect each instrument 10 that has been opened or otherwise experienced a breach of the primary chamber 14.

Hygienic requirements of pharmaceutical, food, and biotechnical manufacturing require that equipment be easily cleaned. The equipment must additionally not contain cavities that could harbor hazardous bacteria, and present a difficulty to cleaning and inspection. Pressure switches 54 usually contain such objectionable cavities. Accordingly, the pressure switches 54 should not be exposed to the exterior of the housing 12. According to embodiments of the present invention, exposing the low pressure side of pressure switches 54 to the reference chamber 16, rather than externally of the housing 12, qualifies the analytical instrument 10 for use in these hygienic environments.

Another benefit of locating the pressure switches 54 in the bulkhead 18 between the primary chamber 14 and reference chamber 16 is that the switches 54 are not exposed to the external environment. Accordingly, low-cost, commercially available switches 54 may be utilized. Pressure switches 54 that are qualified for use in hazardous environments (e.g., exposure to caustic chemicals, flammable gases, excessive moisture, and the like) are very expensive and more difficult to obtain than off-the-shelf pressure switches 54.

A further benefit of the primary chamber 14 and reference chamber 16 sharing a bulkhead 18 between them is thermal coupling. A change in temperature, such as by cooling parts of the instrumentation system 20 for improved performance, can alter the pressure in the sealed primary chamber 14. By thermally coupling the reference chamber 16 to the primary chamber 14 via a common, thermally conductive bulkhead 18, pressure changes in the two chambers 14, 16 due to temperature are similar, minimizing the change in differential pressure. Additionally, in embodiments in which parts of the instrumentation system 20 are cooled, the low dew point of the inert gas, such as nitrogen, filling the primary chamber 14 precludes condensation of moisture on the electronics, lenses 22, or other components of the instrumentation system 20.

As described above, a safety valve 44 may be disposed, in some embodiments, between the primary chamber 14 and the reference chamber 16. The relief pressure of the safety valve 44 is rated for the maximum pressure of inert gas to be established in the primary chamber 14, and is preferably higher than the minimum pressure of inert gas that will maintain the minimum predetermined pressure differential to the reference chamber 16 (thus providing some "headroom" of pressure to accommodate slow leaks and system tolerances). The purpose of the safety valve 44 is to protect components of the instrumentation system 20 that may be damaged by over-pressurization. Additionally, an excessive inert gas pressure in the primary chamber 14 may itself present a hazard of explosion, if it places mechanical stresses on the housing 12 that exceed its structural integrity.

One potential problem with a safety valve 44 is that typical poppet style safety valves 44 may malfunction by leaking at pressures lower than their relief pressure. In this case, inert gas, and concomitant pressure, would leak from the primary chamber 14 into the reference chamber 16, reducing the pressure differential. A sufficient leak would eventually cause the differential pressure to drop below the predetermined amount, tripping the pressure switches 54 and shutting down the instrumentation system 20. In one embodiment, an elastomeric strut 60 affixed to the interior of the cover 46 is positioned so as to contact, and seal, the safety valve 44 when the cover 46 is affixed to the housing 12. Although this disables the functionality of the safety valve 44, it does so only during operation of the analytic instrument 10. During charging of the primary chamber 14 with inert gas—i.e., at manufacture and during service—the cover 46 must be removed to charge the primary chamber 14 via the fill valve 42. The safety valve 44 is thus operative during pressurization operations to prevent over-pressurization. Following pressurization of the primary chamber 14 with inert gas (even if the safety valve operated properly to limit the maximum pressure), when the cover 46 is attached to the housing 12, the safety valve 44 functionality is no longer necessary, and potential leaks through the safety valve 44 can be safely prevented by "plugging" it with the elastomeric strut 60.

Figure 2:
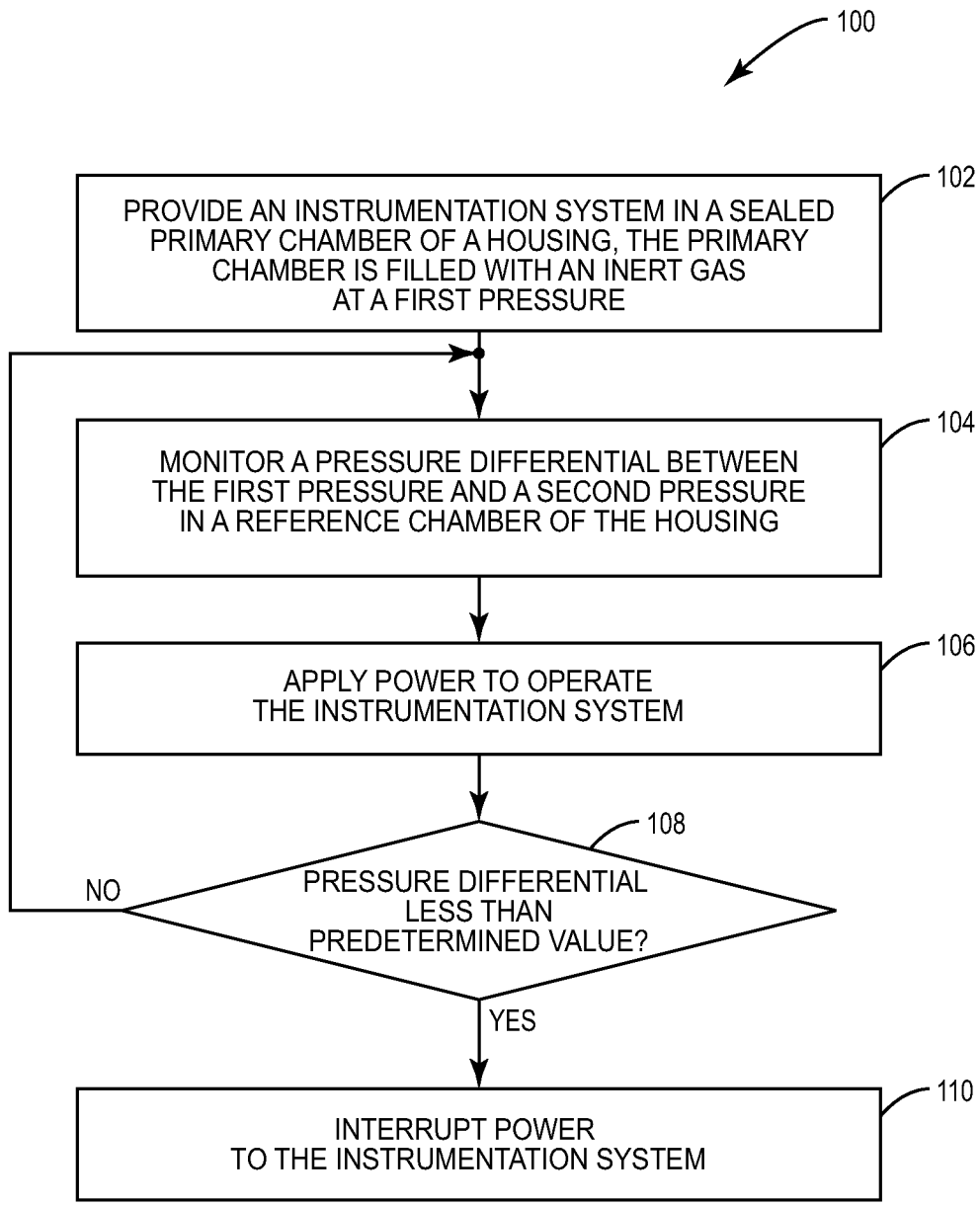
FIG. 2 is a flow diagram of a method of operating an analytical instrument in a hazardous environment.

FIG. 2 depicts a method 100 of operating an analytical instrument in a hazardous environment. Initially, an instrumentation system 20 is provided in a sealed primary chamber 14 of a housing 12, wherein the primary chamber 14 is filled with an inert gas at a first pressure (block 102). A pressure differential between the first pressure and a second pressure in a reference chamber 16 of the housing 12 is monitored (block 104), such as by pressure switches 54 disposed between, and in pressure-sensing relationship with, the two chambers 14, 16. Power is applied to operate the instrumentation system 20 (block 106). If the monitored the pressure differential falls below a predetermined value (block 108), then power to the instrumentation system 20 is interrupted (block 110). Otherwise, the pressure differential continues to be monitored (block 104), and power continues to be applied to the instrumentation system 20 (block 106).

Embodiments of the present invention provide numerous advantages over the prior art. By maintaining a static pressure of inert gas over the instrumentation system 20, the analytical instrument 10 may be deployed in hazardous environments, such as NEC C1D1, without the need for bulky and costly on-site nitrogen purge and dynamic pressurization tanks and associated equipment. The inert gas additionally prevents condensation. Fire safety is ensured without the constant flow of inert gas by monitoring the static pressure of inert gas in the primary chamber 14, and interrupting power to all electronics if the pressure drops, such as if the housing 12 is opened. This safety feature also enforces laser safety regulations. To enable the use of inexpensive pressure switches 54 and comply with the hygienic requirements of some manufacturing environments, a reference chamber 16 provides a protected, lower-pressure zone, which in some embodiments may be filled with atmospheric air at ambient atmospheric pressure. Pressure monitors within the primary chamber 14 may log long-term trends in pressurization, and provide inherent evidence of tampering. By co-locating a fill valve 42 and safety valve 44, and requiring access to the reference chamber 16 to pressurize the primary chamber 14 with inert gas, the safety valve 44 may perform an overpressure prevention function, and may be safely plugged during operative use to prevent inadvertent leakage from the primary chamber 14.

The present invention may, of course, be carried out in other ways than those specifically set forth herein without departing from essential characteristics of the invention. The present embodiments are to be considered in all respects as illustrative and not restrictive, and all changes coming within the meaning and equivalency range of the appended claims are intended to be embraced therein.

What is claimed is:

1. An analytical instrument, comprising:
   a housing comprising a sealed primary chamber filled with an inert gas at a first pressure, and separated by a bulkhead from a reference chamber filled with gas at a second pressure lower than the first pressure by a predetermined pressure differential;
   an instrumentation system disposed in the primary chamber;
   a power delivery network operative to provide electrical power to the instrumentation system; and
   a first pressure switch disposed in the bulkhead between the primary and reference chambers and connected to the power delivery network, the first pressure switch operative to interrupt power to the instrumentation system if the pressure differential falls below the predetermined level.

2. The analytical instrument of claim 1, wherein the reference chamber is filled with atmospheric air and wherein the second pressure is atmospheric pressure.

3. The analytical instrument of claim 2, wherein the reference chamber comprises the exterior of the housing.

4. The analytical instrument of claim 2, wherein the reference chamber is sealed, and further comprising an equalization port disposed in the housing between the reference chamber and the housing exterior, the equalization port operative to exchange air but prevent the ingress of external moisture or contaminants into the reference chamber.

5. The analytical instrument of claim 1, further comprising a second pressure switch disposed in the bulkhead between the primary and reference chambers and connected to the power delivery network, the second pressure switch operative to interrupt power to the instrumentation system if the pressure differential falls below the predetermined level and the first pressure switch fails to interrupt the power.

6. The analytical instrument of claim 5, wherein the first and second pressure switches are connected in series, and wherein the series connection of pressure switches is interposed between at least part of the power delivery network and the instrumentation system.

7. The analytical instrument of claim 1, further comprising one or more pressure sensors disposed in the primary chamber and operative to monitor the first pressure.

8. The analytical instrument of claim 1, further comprising a one-way fill valve disposed in the housing and operative to inject inert gas into the primary chamber.

9. The analytical instrument of claim 8, further comprising one or more release valves disposed in the housing, spaced apart from the fill valve, and operative to bleed gas from the primary chamber at least when purging the primary chamber with the inert gas.

10. The analytical instrument of claim 8, further comprising a safety valve disposed in the housing and operative to prevent over-pressurization of the primary chamber by bleeding, from the primary chamber, gas at a pressure above a predetermined delta over the first pressure.

11. The analytical instrument of claim 10, wherein the one-way fill valve and the safety valve are disposed in the bulkhead between the primary and reference chambers.

12. The analytical instrument of claim 11, further comprising an elastomeric strut disposed in the reference chamber and operative to seal the safety valve against leaking pressure from the primary chamber when the reference chamber is sealed from the exterior of the housing.

13. The analytical instrument of claim 1, wherein the instrumentation system comprises a Raman spectroscopy system.

14. The analytical instrument of claim 1, wherein the Raman spectroscopy system comprises a free space optical system comprising:
   an excitation laser beam source disposed in the primary housing;
   optical path components disposed in the primary housing; and
   an optical detector disposed in the primary housing;
   wherein optical path components project the excitation laser beam through a transparent window in the primary housing to impinge on or within a sample, and Raman scattered photons from the sample entering the window are processed by the optical path components and detected by the detector.

15. A method of operating an analytical instrument in a hazardous environment, comprising:
   providing an instrumentation system in a sealed primary chamber of a housing, the primary chamber filled with an inert gas at a first pressure;
   monitoring a pressure differential between the first pressure and a second pressure in a reference chamber of the housing;
   applying power to operate the instrumentation system;
   sensing that the pressure differential falls below a predetermined value; and
   in response to the decrease in pressure differential, interrupting power to the instrumentation system.

16. The method of claim 15 further comprising monitoring one or more pressure sensors in the primary chamber and maintaining a log of primary chamber pressure values.

17. The method of claim 16 further comprising, following an interruption of power to the instrumentation system and a re-pressurization of the primary chamber with inert gas:
   re-applying power to the instrumentation system only upon the successful completion of a cryptographic verification process.

18. The method of claim 15 wherein sensing that the pressure differential falls below a predetermined value and interrupting power to the instrumentation system comprises:
   providing a pressure switch disposed in a bulkhead between the primary and reference chambers and connected to a power delivery network operative to supply power to the instrumentation system;
   wherein the pressure switch is operative to interrupt power to the instrumentation system if the pressure differential falls below the predetermined level.

* * * * *